United States Patent [19]

Minamino et al.

[11] 4,424,204

[45] Jan. 3, 1984

[54] CREAMY OR MILKY SKIN COSMETIC COMPOSITIONS

[75] Inventors: Hiromi Minamino; Mitsuo Kondo; Yasuhisa Otani, all of Odawara; Akira Miyashita, Yokohama; Kenzo Okada, Tokyo; Takashi Kuramoto, Onomichi, all of Japan

[73] Assignees: Kanebo Ltd.; Maruzen Kasei Co., Ltd., both of Japan

[21] Appl. No.: 241,525

[22] Filed: Mar. 9, 1981

[30] Foreign Application Priority Data

Mar. 8, 1980 [JP] Japan .................................. 55-29607
Oct. 2, 1980 [JP] Japan ................................. 55-138511

[51] Int. Cl.$^3$ ...................... A61K 7/021; B01J 13/00; C07G 3/00; C07H 15/00
[52] U.S. Cl. ............................... 424/63; 252/DIG. 5; 424/168; 424/358; 424/361; 424/362; 424/363; 424/364; 424/365; 536/18.1
[58] Field of Search ...................... 536/4, 18.1; 424/63

[56] References Cited

U.S. PATENT DOCUMENTS

| | | |
|---|---|---|
| 3,046,195 | 7/1962 | Zagt, Jr. ................................ 536/4 |
| 3,066,072 | 11/1962 | Gottfried et al. ....................... 536/4 |
| 3,110,711 | 11/1963 | Wagner et al. .......................... 536/4 |
| 3,164,581 | 1/1965 | Murager ................................ 536/4 |
| 3,240,775 | 3/1966 | Schweiger .............................. 536/4 |
| 3,442,911 | 5/1969 | Baxendale .............................. 536/4 |
| 3,450,691 | 6/1969 | Wagner et al. .......................... 536/4 |
| 3,629,231 | 12/1971 | Hough et al. ........................... 536/4 |
| 3,812,097 | 5/1974 | Baran et al. ............................ 536/4 |
| 4,107,425 | 8/1978 | Pfeffer et al. .......................... 536/4 |
| 4,278,657 | 7/1981 | Tezuka et al. .......................... 424/63 |

FOREIGN PATENT DOCUMENTS

| | | | |
|---|---|---|---|
| 1157604 | 11/1963 | Fed. Rep. of Germany .......... 536/4 |
| 1301851 | 7/1962 | France .................................. 536/4 |
| 41-16398 | 9/1966 | Japan .................................... 536/4 |

OTHER PUBLICATIONS

Beaton et al., J. Chem. Soc., (London), 1955, part 3, pp. 3126–3129.
Martindale, 26th Edition, 1972, The Extra Pharmacopoeia, pp. 563, 714, 715.

*Primary Examiner*—Dale R. Ore
*Attorney, Agent, or Firm*—McGlew and Tuttle

[57] ABSTRACT

Disclosed is a creamy or milky skin cosmetic composition which contains an emulsifying agent comprising an 18α-glycyrrhizin (18α-glycyrrhizic acid or its sodium, potassium or ammonium salt) that is a novel compound derived from a conventional glycyrrhizin (i.e., any form of 18β-glycyrrhizin extracted from licorice root) or a glycyrrhizin composition consisting of an 18α-glycyrrhizin and an 18β-glycyrrhizin. This skin cosmetic composition causes no irritation to the skin and hence has great safety for the skin, as contrasted with skin cosmetic compositions using synthetic emulsifiers. Moreover, it exhibits very good emulsion stability and storage stability and presents a very attractive appearance (fine texture and good gloss) owing to the unique effects of the 18α-glycyrrhizin. In particular, this skin cosmetic composition is characterized in that the difficulties inherent in the use of an emulsifying agent comprising an 18β-glycyrrhizin alone (i.e., the fact that the resulting emulsion is subject to gelation, requires a long time for defoaming, and may undergo a considerable change in viscosity when transferred by the application of a shear stress) are overcome.

22 Claims, No Drawings

CREAMY OR MILKY SKIN COSMETIC COMPOSITIONS

BACKGROUND OF THE INVENTION (1) Field of the Invention

This invention relates to creamy or milky skin cosmetic compositions which contain an emulsifying agent comprising an 18α-glycyrrhizin that is a novel compound obtained by isomerization of a conventional glycyrrhizin (i.e., any form of 18β-glycyrrhizin extracted from licorice root) or a glycyrrhizin composition consisting of an 18α-glycyrrhizin and an 18β-glycyrrhizin. More particularly, it relates to such creamy or milky skin cosmetic compositions which cause no irritation to the skin, exhibit good emulsion stability and storage stability (stability to aging), present an attractive appearance (fine texture and good gloss), require only a short time for defoaming subsequent to the emulsification step during manufacture (that is, are easy to defoam), and undergo little change in viscosity when subjected to a shear stress. Still more particularly, it relates to such creamy or milky skin cosmetic compositions in which the difficulties inherent in the use of an emulsifying agent comprising an 18β-glycyrrhizin alone are overcome.

(2) Description of the Prior Art

It is well known in the prior art that skin cosmetics of the emulsion type, such as creams and milky lotions, are required to sasify the following conditions:

(1) They must not cause any irritation to the skin and, hence, must have great safety for the skin.
(2) They must have good emulsion stability and storage stability.
(3) They must have good chemical stability including high resistance to hydrolysis.
(4) They must present an attractive appearance from the viewpoints of texture and gloss.
(5) They must have great affinity for the skin.

In order to meet these requirements, elaborate compositional designs are being made, for example, by selection of suitable emulsifying agents, search for useful combinations thereof, and concomitant use of special materials. However, it is not easy to accomplish this purpose. Specifically, it is very difficult to satisfy the above-described conditions by using a single emulsifying agent.

For example, nonionic surface-active agents of the polyoxyethylene alkyl ether type are strongly irritative to the skin and poor in emulsifying power. Nonionic surface-active agents of the ester type, such as polyoxyethylene fatty acid esters, polyoxyethylene glycerol fatty acid esters, polyoxyethylene sorbitan fatty acid esters and the like, are poor in emulsifying power and resistance to hydrolysis.

Anionic surface-active agents, such as sulfuric esters of higher alcohols, alkylarylsulfonic acid salts, higher fatty acid salts and the like, have a strong degreasing power and cause irritation to the skin.

Cationic surface-active agents and ampholytic surface-active agents are also irritative to the skin.

On the other hand, conventional glycyrrhizins (i.e., 18β-glycyrrhizins within the scope of the general formula (2) which will be given later) are disadvantageous in that they have only a weak emulsifying power, their acidic aqueous solutions having a pH value of 5.5 or less are subject to gelation, and the emulsions obtained therewith are hard to defoam. Thus, it is quite impossible to obtain creams or milky lotions having good emulsion stability and storage stability by using a conventional glycyrrhizin (hereinafter referred to as an 18β-glycyrrhizin) as the emulsifying agent.

Karaya gum, locust bean gum, xanthan gum and the like are characterized by thickening properties, but are poor in emulsifying power. Thus, they cannot provide any practical emulsion stability, as will be described later.

Pectin has a somewhat better emulsifying power than karaya gum, locust bean gum, xanthan gum and the like. Nevertheless, the use of pectin alone as the emulsifying agent hardly produces emulsions having good emulsion stability and storage stability.

Prior to this invention, Yasuhisa Otani and others who are among the present inventors have discovered that skin cosmetic compositions of the emulsion type which cause no irritation to the skin and hence have great safety for the skin, exhibit excellent emulsion stability and storage stability, and present an attractive appearance (fine texture and good gloss) can be obtained by using an emulsifying agent composed of an 18β-glycyrrhizin (i.e., a conventional glycyrrhizin) and a water-soluble polysaccharide such as pectin or the like (U.S. patent application, Ser. No. 52,263, filed June 26, 1979, now U.S. Pat. No. 4,278,657 issued July 14, 1981; British patent application No. 7,920,803 filed June 14, 1979; and French Patent Application No. 7,916,622 filed June 27, 1979). The creamy or milky skin cosmetic compositions prepared in accordance with the aforesaid invention are of high quaity, but involve considerable difficulties. Specifically, they require a long time for defoaming subsequent to the emulsification step during manufacture, because a large amount of stable foam is formed owing to the effect of the 18β-glycyrrhizin and pectin. Moreover, especially in the case of products having high viscosity or consistency, they may undergo a change in viscosity or consistency when subjected to a shear stress (for example, when forced into containers by means of a cylinder pump type filling machine or the like).

In order to overcome the above-described difficulties, the present inventors have performed intensive and extensive studies and have discovered that all of the difficulties (i.e., the fact that the prior art skin cosmetic compositions are hard to defoam and may undergo a viscosity drop when subjected to a heavy shear stress) can be overcome by using an 18α-glycyrrhizin (i.e., a glycyrrhizin within the scope of the structural formula (1) which will be given later) or a specific glycyrrhizin composition consisting of an 18α-glycyrrhizin and an 18β-glycyrrhizin (selected from among the novel compounds and compositions recently invented by Akira Miyashita, Kenzo Okada and Takashi Kuramoto) in place of the 18β-glycyrrhizin. In addition, they have also discovered that creamy or milky skin cosmetic compositions of fairly high quality can be obtained without using any water-soluble polysaccharides (such as pectin and the like) concomitantly. The present invention is based on these discoveries.

SUMMARY OF THE INVENTION

It is an object of the present invention to provide a creamy or milky skin cosmetic composition which exerts a mild action on the skin without causing irritation thereto, has great affinity for the skin, exhibits excellent storage stability and emulsion stability, and presents an attractive appearance (fine texture and good gloss).

It is another object of the present invention to provide novel emulsifying agents.

It is still another object of the present invention to provide a skin cosmetic composition of the acidic emulsion type which does not use any synthetic surface-active agents, permits easy design of its formulation (or chemical makeup), and can be readily and advantageously prepared on an industrial scale.

The above and other objects of the invention are accomplished by a creamy or milky skin cosmetic composition which consists essentially of an emulsifying agent, an oily substance and water, the emulsifying agent comprising at least one 18α-glycyrrhizin of the structural formula

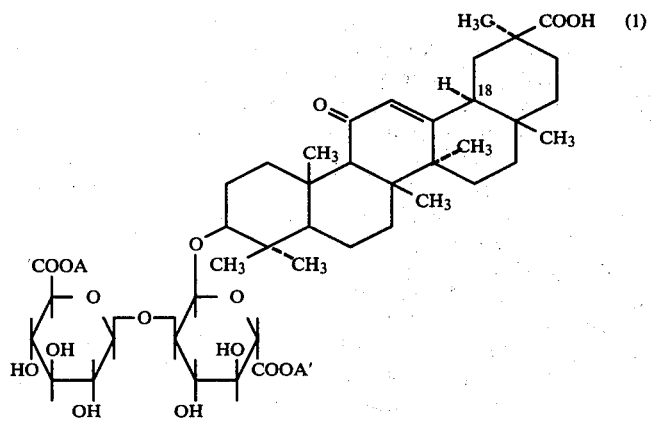

where A and A' independently represent hydrogen atoms, sodium atoms, potassium atoms or ammonium groups, or a glycyrrhizin composition consisting of from 10 to 98 mole % of an 18α-glycyrrhizin as defined above and from 2 to 90 mole % of an 18β-glycyrrhizin of the structural formula

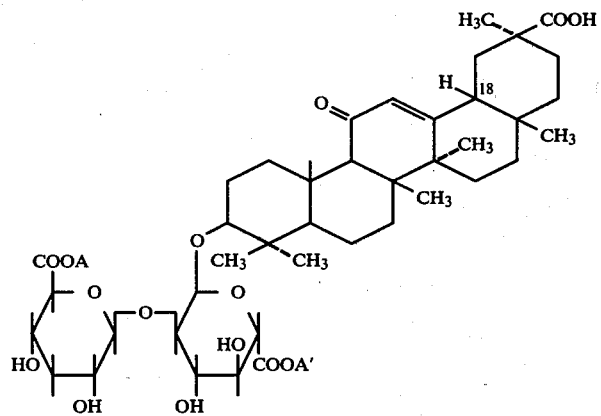

where A and A' independently represent hydrogen atoms, sodium atoms, potassium atoms or ammonium groups.

DETAILED DESCRIPTION OF THE PREFERRED EMBODIMENTS

The 18α-glycyrrhizins which are within the scope of the structural formula (1) given above and can be used in the practice of the present invention are novel compounds and disclosed in Japanese Patent Application No. 24023/'80 filed Feb. 29, 1980. Similarly, the glycyrrhizin compositions which consist of from 10 to 98 mole % of an 18α-glycyrrhizin as described above and from 2 to 90 mole % of an 18β-glycyrrhizin within the scope of the structural formula (2) given above and can be used in the practice of the present invention are novel compositions and disclosed in Japanese Patent Application No. 580/'80 filed Jan. 9, 1980. These compounds and compositions were invented by Akira Miyashita, Kenzo Okada and Takashi Kuramoto who are among the present inventors, and applications for patent on these inventions have been filed in Japan (as described above), U.S.A., Great Britain and France, the corresponding common U.S. application thereto bearing U.S. Ser. No. 220,880 and having a filing date of Jan. 8, 1981.

As can be seen from the structural formula (1) given above, the aforesaid 18α-glycyrrhizins are different from conventional glycyrrhizins (i.e., the glycyrrhizins within the scope of the structural formula (2)) only in that the hydrogen atoms located at the 18-position has the α-configuration. (In order to distinguish between these novel glycyrrhizins and conventional glycyrrhizins extracted from licorice root, the former compounds are herein referred to as 18α-glycyrrhizins and the latter ones as 18β-glycyrrhizins.)

While 18α-glycyrrhizins have some properties in common with 18β-glycyrrhizins, they also show such peculiar properties as cannot be expected from the slight structural difference consisting in the distinct steric configuration of only one hydrogen atom.

The main properties of 18α-glycyrrhizins are described below in comparison with those of 18α-glycyrrhizins. All of the 18α-glycyrrhizin samples appearing in the following description are those prepared in the examples which will be given later.

(a) Melting point (decomposition point)

Glycyrrhizins show no melting point. The decomposition points of typical 18α- and 18β-glycyrrhizins are as follows:

| Sample | 18α-Isomer | 18β-Isomer |
| --- | --- | --- |
| Free acid | 206° C. | 210° C. |
| Monoammonium salt | 212–213° C. | 216° C. |
| Monopotassium salt | 248° C. | 246° C. |

(b) Specific optical rotation $[\alpha]_D^{20}$ (as measured with a 1%(w/v) solution in 50%(v/v) ethanol)

| Sample | 18α-Isomer | 18β-Isomer |
| --- | --- | --- |
| Free acid | +26.1° | +60.4° |
| Monoammonium salt | +23.2° | +57.1° |
| Monopotassium salt | +23.0° | +56.0° |

(c) Ultraviolet absorption spectrum

Measurements were made of the ultraviolet absorption spectra of 18α- and 18β-glycyrrhizic acid monoammonium salt dissolved in 50%(v/v) ethanol. The values for $\lambda_{max}$, $E_{1cm}^{1\%}$ and $\epsilon$ are as follows:

| | 18α-Isomer | 18β-Isomer |
| --- | --- | --- |
| $\lambda_{max}$ | 246 nm | 251 nm |
| $E_{1cm}^{1\%}$ | 128.7 | 136.0 |
| $\epsilon$ | 10,810 | 11,420 |

(d) Infrared absorption spectrum

The results obtained with KBr tablets indicate that there is no appreciable difference between an 18α-isomer and its corresponding 18β-isomer.

(e) Solubility

Monopotassium, monosodium, monoammonium, disodium, dipotassium and diammonium salts are easily soluble in water and sparingly soluble in methanol and ethanol. (The solubility and dissolution rate of an 18α-isomer are both superior to those of its corresponding 18β-isomer.) Free acid is easily soluble in methanol, ethanol, dioxane and acetone and slightly soluble in water.

(f) Solution properties

The solution properties of 18α-isomers are significantly different in many respects from those of 18β-isomers, as described below in detail.

(i) Aqueous solutions of 18α-isomers are stable even in the acidic pH range where 18β-isomers would induce gelation. This can be seen in Table 1 showing the viscosities of an aqueous solution of monosodium salt at various pH values. Similar differences can be recognized with regard to other salts than monosodium salt.

TABLE 1

| Sample | 18α-Isomer | | 18β-Isomer | |
| --- | --- | --- | --- | --- |
| Concentration | 0.5% | 2.0% | 0.5% | 2.0% |
| pH 6.0 | 1.06 | 1.07 | 1.07 | 1.20 |
| 5.5 | 1.07 | 1.10 | 1.07 | >30 |
| 5.0 | 1.07 | 1.07 | 2.03 | >30 |

TABLE 1-continued

| Sample | 18α-Isomer | | 18β-Isomer | |
| --- | --- | --- | --- | --- |
| Concentration | 0.5% | 2.0% | 0.5% | 2.0% |
| 4.5 | 1.05 | 1.10 | >30 | >30 |
| 4.0 | 1.03 | 1.03 | >30 | >30 |

Note:
The pH values of the test solutions were adjusted with 1N NaOH or 1N HCl. Their viscosities were measured at 20° C. with an Ubbelohde viscometer and expressed in centipoises (cps).

(ii) Aqueous solutions of an 18α- and an 18β-isomer are placed in test tubes, foamed by shaking the test tubes under the same conditions, and allowed to stand. Then, as can be seen from the data of Table 2, the aqueous solution of the 18α-isomer shows a much higher rate of foam disappearance than that of the 18β-isomer does. (However, there is no appreciable difference in foaming properties.)

TABLE 2

| Time elapsed | Rate of foam disappearance (%) | |
| --- | --- | --- |
| (minutes) | 18α-Isomer | 18β-Isomer |
| 10 | 46.0 | 20.0 |
| 30 | 82.1 | 25.1 |
| 60 | 88.5 | 26.5 |
| 90 | 91.0 | 28.7 |

Note:
The test solutions were 0.5% aqueous solutions of 18α- and 18β-glycyrrhizic acid monopotassium salt. The rate of foam disappearance was calculated from the height of the foam.

The aforesaid 18α-glycyrrhizins can be prepared in the following manner: Any form of 18β-glycyrrhizin extracted from licorice root is dissolved in water or alcohol and heated in the presence of alkali to convert the 18β-glycyrrhizin into an 18α-glycyrrhizic acid salt. Then, 18α-glycyrrhizic acid can be obtained by isolating the resulting 18α-glycyrrhizic acid salt from the reaction mixture in the form of free acid. Subsequently, the free acid thus obtained may be converted into a salt as desired.

The chemical structure of 18α-glycyrrhizins can be confirmed in the following manner:

(1) Elemental analysis provides substantially the same values as calculated on the assumption that 18α-glycyrrhizins are isomeric with 18β-glycyrrhizins. Some examples of analytical data are given below.

| | Calculated | Found |
| --- | --- | --- |
| (i) Free acid | | |
| C | 61.30% | 61.10% |
| H | 7.59% | 7.62% |
| (ii) Monoammonium salt | | |
| C | 60.01% | 60.32% |
| H | 7.80% | 7.70% |
| N | 1.67% | 1.61% |

(2) Hydrolysis of an 18α-glycyrrhizin with 10% sulfuric acid produces glycyrrhetinic acid in which the hydrogen atom located at the 18-position has the α-configuration (hereinafter referred to as 18α-glycyrrhetinic acid) and glucuronic acid. Similarly, hydrolysis of an 18β-glycyrrhizin produces glycyrrhetinic acid in which the hydrogen atom located at the 18-position has the β-configuration (hereinafter referred to as 18β-glycyrrhetinic acid) and glucuronic acid. Thus, the hydrolysis product of an 18α-glycyrrhizin differs from that of an 18β- glycyrrhizin only in the steric configuration of the hydrogen atom located at 18-position of the glycyrrhetinic acid. (It is to be understood that 18α-glycyrrhetinic acid is a well-known compound and can be identified by comparison with an authentic sample.)

(3) The molar ratio of glucuronic acid to 18α-glycyrrhetinic acid present in the aforesaid hydrolysis product of an 18α-glycyrrhizin is 2:1. (In addition, the acid hydrolysis product of 18β-glycyrrhizic acid has been analyzed. The molar ratio of glucuronic acid to 18β-glycyrrhetinic acid present therein is also 2:1, which agrees with the theoretical value.)

(4) When subjected to a chemical pocess comprising methylation with methyl iodide, reduction with LiAlH₄, remethylation and methanolysis, an 18α-glycyrrhizin produces only two methylated sugars of the structural formulas

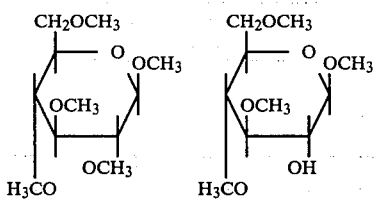

This result agrees with that obtained by subjecting an 18β-glycyrrhizin to the same chemical process.

The above-described analytical results indicate that both the aglycone moiety and the glucuronic moiety of the novel compound obtained by treating an 18β-glycyrrhizin with alkali are in no way different from those of the 18β-glycyrrhizin, except for the steric configuration of the hydrogen atom located at the 18-position which is the α-configuration in the novel compound as contrasted with the β-configuration in the original compound.

In order to examine the toxicity of 18α-glycyrrhizins, a typical 18α-glycyrrhizin (i.e., 18α-glycyrrhizic acid monoammonium salt) was subjected to the following tests.

1. General Toxicity Test (1) Acute Toxicity Test

Ten female and ten male mice of the ICR strain (weighing 18–20 g and 23–25 g, respectively) were employed in this test. The 18α-glycyrrhizin was orally administered to each animal in a dose of 2.4 g/kg. As a result, none of the animals died. Moreover, no toxic symptoms were noted in all animals. (For details, see Draize, J. H. "Appraisal of the Safety of Chemicals in Foods, Drugs and Cosmetics", Associations of Food and Drug Officials of the United States.)

II. Specific Toxicity Tests (1) Temporary Skin Irritation Test

Six female rabbits of the New Zealand white strain (weighing 2.4–2.6 kg) were employed in this test. According to the closed patch test technique, 10%, 1% and 0.1% aqueous solutions of the 18α-glycyrrhizin were applied to the animals. When rated by Draize's method, the temporary irritation score was 0 at every concentration.

(2) Continuous Skin Irritation Test

Three female rabbits of the New Zealand white strain (weighing 2.7–2.9 kg) were employed. This test was performed over a period of 4 weeks, during which 25%, 2.5%, 0.25% and 0% aqueous solutions of the 18α-glycyrrhizin were continually applied to the dorsal skin (intact and injured skin areas) of the animals. The degree of irritation was rated by Draize's method. At each concentration, no abnormalities were noted in the intact and injured skin areas throughout the test period.

III. Human Patch Test

Eighteen male and five female healthy human subjects were employed in this test. According to the closed patch test technique, 10%, 1% and 0.1% aqueous solutions of the 18α-glycyrrhizin were applied to the subjects and the degree of irritation was examined after 24 hours. At each concentration, no abnormalities were noted in all cases.

Next, the glycyrrhizin compositions which can be used in the practice of the present invention are described in more detail.

These glycyrrhizin compositions can be prepared in the following manner: Any form of 18β-glycyrrhizin extracted from licorice root is dissolved in water or alcohol and heated in the presence of an alkali to convert from 10 to 98 mole % of the 18β-glycyrrhizin into an 18α-glycyrrhizic acid salt. Then, a glycyrrhizic acid composition can be obtained by isolating the resulting 18-glycyrrhizic acid salt, together with the unconverted 18β-glycyrrhizin, from the reaction mixture in the form of free acid. Subsequently, the free acid thus obtained may be converted into a salt (a sodium, potassium or ammonium salt) as desired.

As stated before, the properties of 18α-glycyrrhizins are markedly different from those of 18β-glycyrrhizins. However, it has surprisingly been found that, just like 18α-glycyrrhizins in pure form, mixtures of an 18α-glycyrrhizin and an 18β-glycyrrhizin provide aqueous solutions which are stable even in an acidic pH range, so long as the mixture have an 18α-glycyrrhizin content of not less than 10 mole % and preferably not less than 30 mole %. Moreover, these aqueous solutions do not undergo gelation even in an acidic pH range (i.e., in the pH range of from 2.0 to 6.0). Furthermore, such mixtures of an 18α-glycyrrhizin and an 18β-glycyrrhizin (i.e., the above-defined glycyrrhizin compositions) have beneficial properties which are substantially the same as those of pure 18α-glycyrrhizins. In addition, these glycyrrhizin compositions are advantageous in that they are less expensive and more economical than pure 18α-glycyrrhizins and require no viscosity modifiers in the preparation of clear liquid skin cosmetic compositions having high viscosity.

Table 3 comparatively shows some properties (i.e., solution viscosity, solution turbidity, dissolution time, and rate of foam disappearance in solution) of glycyrrhizin compositions (having various 18α-glycyrrhizin contents), pure 18α-glycyrrhizins and pure 18β-glycyrrhizins.

TABLE 3

| Sample Form | 18α-Isomer content (%) | Solution viscosity (cps) | Solution turbidity (ppm) | Dissolution time (sec) | Rate of foam dissappearance in solution (%) |
|---|---|---|---|---|---|
| A | 0 | >30 | 59.5 | 660 | 29.0 |
| K | 0 | >30 | 87.1 | 490 | 28.7 |
| N | 0 | >30 | 87.0 | 480 | 28.8 |
| A | 30 | 2.01 | 0.5 | 60 | 29.1 |
| K | 30 | 2.05 | 0.6 | 32 | 29.2 |
| N | 30 | 2.05 | 0.6 | 32 | 29.3 |
| A | 50 | 1.08 | 0.3 | 60 | 89.4 |
| K | 50 | 1.09 | 0.3 | 30 | 89.5 |
| N | 50 | 1.09 | 0.3 | 30 | 89.5 |

TABLE 3-continued

| Sample Form | 18α-Isomer content (%) | Solution viscosity (cps) | Solution turbidity (ppm) | Dissolution time (sec) | Rate of foam disappearance in solution (%) |
|---|---|---|---|---|---|
| A | 70 | 1.06 | 0.3 | 58 | 89.6 |
| K | 70 | 1.05 | 0.4 | 30 | 89.7 |
| N | 70 | 1.05 | 0.4 | 30 | 89.8 |
| A | 80 | 1.09 | 0.3 | 57 | 90.1 |
| K | 80 | 1.08 | 0.4 | 30 | 90.2 |
| N | 80 | 1.08 | 0.4 | 30 | 90.3 |
| F | 80 | 1.09 | 0.4 | | |
| A | 98 | 1.07 | 0.3 | 55 | 90.7 |
| K | 98 | 1.07 | 0.3 | 31 | 90.8 |
| N | 98 | 1.07 | 0.3 | 31 | 90.8 |
| A | 100 | 1.06 | 0.2 | 53 | 90.8 |
| K | 100 | 1.07 | 0.3 | 32 | 91.0 |
| N | 100 | 1.07 | 0.3 | 32 | 91.1 |
| F | 100 | 1.08 | 0.3 | | |

Notes:
(1) Pure 18β-glycyrrhizins were used when the 18α-isomer content was 0%.
(2) Pure 18β-glycyrrhizins were used when the 18α-isomer content was 100%.
(3) A, N, K and F stand for monoammonium salt, monosodium salt, monopotassium salt and free acid, respectively.
(4) The solution viscosity was determined by adjusting an aqueous solution to pH 5.0 with 1N NaOH or 1N HCl and measuring its viscosity at 20° C. with an Ubbelohde viscometer.
(5) The solution turbidity was determined by subjecting an aqueous solution to direct turbidimetry.
(6) The dissolution time was determined by providing a sample powder having passed through an 80-mesh screen and measuring the time required to dissolve 0.5 g of the powder completely in 100 ml of water under definite stirring conditions.
(7) The rate of foam disappearance in solution was determined by shaking a 0.5% aqueous solution and allowing it to stand for 90 minutes.

Thus, the above-defined 18α-glycyrrhizins and glycyrrhizin compositions have a number of beneficial properties which make it possible to prepare excellent skin cosmetic compositions readily and advantageously on an industrial scale. That is to say:

(1) The above-defined 18α-glycyrrhizins and glycyrrhizin compositions dissolve in water so rapidly that the time required to prepare the skin cosmetic composition of the present invention can be reduced significantly.

(2) The foam which is formed during the preparation of the skin cosmetic composition of the present invention can be destroyed simply by allowing it to stand for a relatively short period of time. Moreover, the time required to defoam the skin cosmetic composition of the present invention is short as compared with similar skin cosmetic compositions prepared using conventional glycyrrhizins alone.

(3) The skin cosmetic composition of the present invention, which is prepared by using any of the above-defined 18α-glycyrrhizins and glycyrrhizin compositions as the emulsifying agent, shows a viscosity slightly higher than the above-described solution viscosity owing to the coexistence of relatively large amounts of cosmetic base materials (such as oily substances and the like). However, the skin cosmetic composition of the present invention is not subject to any appreciable degree of viscosity build-up or gelation even if its pH value is in an acidic range (for example, in the range of from 4 to 6). Moreover, it does not undergo any marked drop in viscosity when subjected to a heavy shear stress. Thus, it is possible to provide creamy or milky skin cosmetic compositions which can be defoamed spontaneously (i.e., by allowing them to stand) and undergo no drop in viscosity when subjected to a shear stress, such skin cosmetic compositions being unable to be realized by the use of any conventional glycyrrhizin.

(4) In the skin cosmetic composition of the present invention, 18α-glycyrrhizin or glycyrrhizin composition is dissolved completely. Moreover, this skin cosmetic composition neither undergoes flocculation or sedimentation nor deteriorates in texture or gloss even after storage for a long period of time (at least 6 months) or freeze (−10° C.)—thaw(30° C.) cycling. Thus, it can retain an attractive appearance (fine texture and good gloss) even under severe temperature conditions. (18β-Glycyrrhizins and certain types of synthetic surface-active agents induce a marked degree of sedimentation or turbidity under similar conditions.)

(5) The above-defined 18α-glycyrrhizins and glycyrrhizin compositions do not induce gelation in any desired pH range and can disperse large amounts of oily substances in water to form a stable emulsion. Moreover, it is unnecessary to select among various synthetic emulsifiers according to their suitability for the intended purpose, as is the case with prior art skin cosmetic compositions of the emulsion type. Thus, in preparing the skin cosmetic composition of the present invention, its formulation can be designed with great ease.

(6) The above-defined 18α-glycyrrhizins and glycyrrhizin compositions are neither toxic nor irritative to the skin in contrast to synthetic surface-active agents, and have as excellent an antiphlogistic effect as conventional glycyrrhizins. It can be expected, therefore, that the skin cosmetic composition of the present invention has beneficial pharmacological effects on the skin.

(7) Owing to the presence of an 18α-glycyrrhizin or glycyrrhizin composition as defined above, not only moderate viscosity and good fluidity but also great affinity for the skin is imparted to the skin cosmetic composition of the present invention. Accordingly, in using this skin cosmetic composition, it can be easily taken out of the container and evenly spread over the skin surface to produce beneficial cosmetic effects. At the same time, the 18α-glycyrrhizin or glycyrrhizin composition present therein exerts a mild action on the skin and produces an antiphlogistic effect, thus giving a non-greasy, smooth and agreeable feeling.

The 18α-glycyrrhizins which are within the scope of the structural formula (1) given above and can be used in the practice of the present invention include 18α-glycyrrhizic acid, or (3β, 18α, 20β)-20-carboxy-11-oxo-30-norolean-12-ene-3-yl-2-O-β-D-glucopyranosyl-α-D-glucopyranosiduronic acid, as well as the monosodium, monopotassium, monoammonium, disodium, dipotassium and diammonium salts thereof.

The 18β-glycyrrhizins (conventional glycyrrhizins) which are within the scope of the structural formula (2) given above include 18β-glycyrrhizic acid, or (3β, 18β, 20β)-20-carboxy-11-oxo-30-norolean-12-ene-3-yl-2-O-β-D-glucopyranosyl-α-D-glucopyranosiduronic acid, as well as the monoammonium, monopotassium, monosodium, disodium, dipotassium and diammonium salts thereof.

In the skin cosmetic composition of the present invention, the above-enumerated 18α-glycyrrhizins may be used alone or in combination.

Where the emulsifying agent present in the skin cosmetic composition of the present invention comprises at least one 18α-glycyrrhizin, it is used in an amount of from 0.01 to 20% by weight and preferably from 0.1 to 3% by weight based on the total weight of the skin cosmetic composition. If the amount is less than 0.01% by weight, the oily substance cannot be emulsified satisfactorily, while if it is greater than 20% by weight, the 18α-glycyrrhizin tends to become less soluble in this system and deposit crystals.

In the glycyrrhizin compositions which consist of an 18α-glycyrrhizin within the scope of the structural formula (1) given above and an 18β-glycyrrhizin within the scope of the structural formula (2) given above and can be used in the practice of the present invention, both components desirably comprise a couple of compounds of the same type which are isometric with each other, for example, 18α-glycyrrhizic acid and 18β-glycyrrhizic acid, 18α-glycyrrhizic acid monopotassium salt and 18β-glycyrrhizic acid monopotassium salt, or the like. More specifically, these glycyrrhizin compositions consist of from 10 to 98 mole % of the 18α-glycyrrhizin and from 2 to 90 mole % of the 18β-glycyrrhizin, and preferably consist of from 30 to 98 mole % of the 18α-glycyrrhizin and from 2 to 70 mole % of the 18β-glycyrrhizin.

Where the emulsifying agent present in the skin cosmetic composition of the present invention comprises such a glycyrrhizin composition, it is used in an amount of from 0.01 to 20% by weight and preferably from 0.1 to 3% by weight based on the total weight of the skin cosmetic composition. If the amount is less than 0.01% by weight, the oily substance cannot be emulsified satisfactorily, while it is greater than 20% by weight, the glycyrrhizin composition tends to become less soluble in this system and deposit crystals.

The oily substances which can be used in the practice of the present invention are well-known oily substances suitable for use in skin cosmetics and include, for example, higher aliphatic hydrocarbons such as liquid paraffin, squalane, vaseline, ceresin, etc.; vegetable fats and oils such as olive oil, almond oil, avocado oil, castor oil, cacao butter, palm oil, etc.; animal fats and oils such as cod liver oil, beef tallow, butter fat, etc.; waxes such as bees wax, carnauba wax, etc.; higher fatty acids such as lauric acid, myristic acid, palmitic acid, stearic acid, oleic acid, behenic acid, lanolin fatty acid, etc.; higher alcohols such as lauryl alcohol, stearyl alcohol, cetyl alcohol, oleyl alcohol, etc.; straight-chain and branched-chain ester oils i.e. other than said fats and oils such as isocetyl myristate butyl stearate, hexyl laurate, octyldodecyl myristate, diisopropyl adipate, diisopropyl sebacate, etc.; silicone oil; and the like. These oily substances may be used alone or in combination. The amount of oily substance used in the skin cosmetic composition of the present invention is in the range of from 15 to 80% by weight and preferably from 20 to 70% by weight based on the total weight of the skin cosmetic composition. If the amount is less than 10% by weight, the resulting skin cosmetic composition has poor emulsion stability, while if it is greater than 80% by weight, the resulting skin cosmetic composition is excessively greasy.

The amount of water used in the skin cosmetic composition of the present invention is in the range of from 10 to 90% by weight and preferably from 20 to 80% by weight based on the total weight of the skin cosmetic composition, whereby to provide a composition of the oil in water (O/W) emulsion type.

The 18α-glycyrrhizin or glycyrrhizin composition which is used in the skin cosmetic composition of the present invention exhibits high surface activity (i.e., good power to reduce interfacial tension) regardless of pH conditions and can thereby disperse the oily substance in water to form a fairly stable emulsion. However, where the oily substance is present in large amounts, it can be very stably emulsified by using an additional emulsifying agent comprising at least one natural surface-active substance selected from the group consisting of lecithin, casein soda, pectin, xanthan gum, karaya gum and locust bean gum. When an 18α-glycyrrhizin or glycyrrhizin composition or a combination of an 18α-glycyrrhizin or glycyrrhizin composition and a natural surface-active substance is used as the emulsifying agent, the foam which is formed in the emulsification step during manufacture is spontaneously destroyed with ease and in a short period of time, as contrasted with prior art skin cosmetic compositions using an emulsifying agent composed of an 18β-glycyrrhizin and a water-soluble polysaccharide (such as pectin or the like) which need be defoamed under reduced pressure during manufacture. Another feature of the present invention is that the skin cosmetic composition of the present invention neither undergoes gelation in a weakly acidic pH range nor produces an extreme degree of structural viscosity, as contrasted with prior art skin cosmetic compositions using an emulsifying agent comprising an 18β-glycyrrhizin alone. Recently, acidic skin cosmetic compositions which have a pH value of around 5 and are mild to the skin have come into common use. The present invention also makes it possible to prepare such acidic skin cosmetic compositions readily. The acidic skin cosmetic compositions thus obtained are not subject to gelation, exhibit good fluidity on the skin, and give an agreeable feeling when applied to the skin. Typically, glycyrrhizic acid provides skin cosmetic compositions having a pH value of from 2.3 to 2.5, its monoalkali metal salts provide ones having a pH value of from 4.5 to 4.6, and its dialkali metal salts provide ones having a pH value of from 5.4 to 5.5.

The above-enumerated surface-active substances may be used alone or in combination. The amount of natural surface-active substance used in the skin cosmetic composition of the present invention is in the range of from 0.1 to 10.0% by weight and preferably from 0.5 to 5% by weight based on the total weight of the skin cosmetic composition.

Where the skin cosmetic composition of the present invention is adapted for use as a massage cream, cleansing cream, skin cream, skin milk or the like, it is unnecessary to incorporate a pigment thereinto. However, where the skin cosmetic composition of the present invention is adapted for use as a foundation cream (under makeup cream) or liquid makeup base (under makeup milky lotion), it is recommended to incorporate a pigment thereinto in addition to the aforesaid ingredients. In this case, the pigment is used in an amount of at most 10% by weight and preferably from 0.5 to 7% by weight based on the total weight of the skin cosmetic composition. The pigments useful for this purpose include inorganic pigments such as titanium oxide, kaolin, yellow oxide of iron, red oxide of iron, black oxide of iron, talc and the like.

Furthermore, if desired, small amounts of cosmetically or pharmacologically effective substances, perfumes, antiseptics and/or colorants may be added thereto.

The creamy or milky skin cosmetic composition of the present invention can be prepared by any well-known procedure. For example, an 18α-glycyrrhizin or a glycyrrhizin composition is dissolved in water by stirring at elevated temperature. While the resulting solution is being stirred, a molten oily substance is added thereto and mixed therewith to form an emulsion.

The creamy or milky skin cosmetic compositions prepared in accordance with the present invention are adaptable for use as massage creams, cleansing creams, skin creams, skin milks, foundation creams (under makeup cream), liquid makeup bases (under makeup milky lotion) and the like.

The creamy or milky skin cosmetic compositions prepared in accordance with the present invention cause no irritation to the skin, have great safety and affinity for the skin, present an attractive appearance characterized by fine texture and good gloss, and exhibit very excellent emulsion stability and storage stability. Owing to the 18α-glycyrrhizin or glycyrrhizin composition present therein, these skin cosmetic compositions are very safe for the skin, are not subject to gelation even under severe conditions (e.g., of pH, content, temperature and the like), and are easy to defoam during manufacture. Moreover, when they are subjected to a heavy shear stress, practically no decrease in viscosity or coarsening of dispersed particles results. Furthermore, these skin cosmetic compositions are easy to handle with the fingers, have excellent fluidity and spreadability on the skin, and exhibit good stability of properties such as texture, gloss, consistency, viscosity, feeling and the like. In addition, when applied to the skin, they give a non-greasy, smooth and agreeable feeling. Thus, these skin cosmetic compositions have a very high commercial value.

The present invention is further illustrated by the following examples. In these examples, all parts and percentages are by weight.

Gloss value was measured according to the method 2 described in JIS-Z8741-1962 (methods for Gloss Measurement).

EXAMPLE 1 (Skin Cream)

(1) Preparation of 18α-Glycyrrhizic Acid Monoammonium Salt

Two hundred parts of 18β-glycyrrhizic acid monoammonium salt (having a purity of 80%) obtained from licorice root was dissolved in 1,000 parts of 4 N NaOH, and the resulting solution was heated under reflux for 8 hours at atmospheric pressure. Thereafter, the pH of the reaction mixture was adjusted to about 2 by the addition of sulfuric acid. The precipitate so formed was extracted with 500 parts of n-hexanol, and the resulting extract was alkalified with aqueous ammonia. After the n-hexanol was distilled off, the residue was recrystallized from 85% methanol to obtain 122 parts of a glycyrrhizic acid monoammonium salt composition (containing 70% of the 18α-isomer).

Then, the 18α-isomer contained therein was separated from the unconverted 18β-isomer in the following manner: A 1% aqueous solution of the aforesaid monoammonium salt was prepared, adjusted to pH 2.0 by the addition of hydrochloric acid, and then filtered through Toyo No. 3 filter paper. The precipitate collected on the filter paper was dissolved in dilute aqueous ammonia to form a 1% solution, which was again adjusted to pH 2.0 by the addition of hydrochloric acid and then filtered. After this procedure (which comprised acidifying the aqueous solution to form a precipitate and separating it by filtration) was repeated four times, the precipitate finally collected on the filter paper was dissolved in concentrated aqueous ammonia. To the resulting solution was added acetic acid (so as to give an acetic acid concentration of about 85%). The 18α-glycyrrhizic acid monoammonium salt which crystallized out of the solution was recrystallized from 80% acetic acid and then from 85% methanol, and further subjected to large-volume preparative high-speed liquid chromatography to remove any trace amounts of glycyrrhizin analogues. Thus, 18α-glycyrrhizic acid monoammonium salt was obtained in a pure form.

(2) Preparation of Skin Cream

| A. Formulation | | |
|---|---|---|
| 1. Cetyl alcohol | 17 | parts |
| 2. Isocetyl myristate | 12 | parts |
| 3. Squalane | 3 | parts |
| 4. Liquid paraffin | 22 | parts |
| 5. Glycyrrhizic acid monoammonium salt composition (18α-isomer: 18β-isomer = 70 mole %: 30 mole %) | 5 | parts |
| 6. Methylparaben | 0.2 | part |
| 7. Propylene glycol | 6 | parts |
| 8. Purified water | 34.6 | parts |
| 9. Perfume | 0.2 | part |

B. Procedure

The oily ingredients 1, 2, 3 and 4 were melted at 80° C. and mixed homogeneously (solution 1). On the other hand, the water-soluble ingredients 5, 6 and 7 were homogeneously dissolved in the ingredient 8 at 80° C. (solution 2). While the solution 2 was being stirred in a homomixer, the solution 1 was added thereto and dispersed therein. The resulting emulsion was allowed to cool and, as soon as a temperature of 70° C. was reached, the ingredient 9 was added thereto. After its temperature dropped to 30° C., the stirring was discontinued. The resulting skin cream was in the form of an O/W emulsion and presented an attractive appearance characterized by fine texture and good gloss (gloss value=90%). It was very stable after 4 months' storage in a thermostatic chamber at 5° C. or 45° C. Moreover, it was also very stable after 6 months' storage at 30° C.

EXAMPLE 2 (Skin Cream)

The procedure of Example 1 was repeated except that the 18α-glycyrrhizic acid monoammonium salt prepared in Example 1 was used in place of the glycyrrhizic acid monoammonium salt composition (18α-isomer:18β-isomer=70 mole %:30 mole %). The resulting skin cream was in the form of an O/W emulsion and presented an attractive appearance characterized by fine texture and good gloss (gloss value=90%). It was very stable after 4 months' storage in a thermostatic chamber at 5° C. or 45° C. Moreover, it was also very stable after 6 months' storage at 30° C.

COMPARATIVE EXAMPLE 1

The procedure of Example 1 was repeated except that 18β-glycyrrhizic acid monoammonium salt was used in place of the glycyrrhizic acid monoammonium salt composition (18α-isomer:18β-isomer=70 mole %:30 mole %). The resulting skin cream formed a gel after 24 hours and then underwent syneresis.

EXAMPLE 3

Preparation of Skin Milk

| A. Formulation | | |
|---|---|---|
| 1. Cetyl alcohol | 5 | parts |
| 2. Octyldodecyl myristate | 1.5 | parts |
| 3. Liquid paraffin | 20.0 | parts |

-continued

| A. Formulation | |
|---|---|
| 4. Pectin* | 20.0 parts |
| 5. Glycyrrhizic acid composition (18α-isomer:18β-isomer = 78 mole %:22 mole %) | 2.0 parts |
| 6. Methylparaben | 0.3 part |
| 7. Purified water | 69.0 parts |
| 8. Perfume | 0.2 part |

*This pectin had a mean molecular weight of 100,000 and a degree of methyl esterification of 65%.

B. Procedure

The ingredients 1, 2 and 3 were melted at 80° C. and mixed homogeneously (solution 1). On the other hand, the ingredients 4, 5 and 6 were homogeneously dissolved in the ingredient 7 at 80° C. (solution 2). While the solution 2 was being stirred in a homomixer, the solution 1 was added thereto and dispersed therein. The resulting emulsion was allowed to cool and, as soon as a temperature of 70° C. was reached, the ingredient 8 was added thereto. After its temperature dropped to 30° C., the stirring was discontinued. The resulting skin cream was in the form of an O/W emulsion which had been spontaneously defoamed to perfection. This skin cream presented an attractive appearance characterized by fine texture and good gloss (gloss value=92%). After 4 months' storage in a thermostatic chamber at 5° C. or 40° C., it was very stable and had excellent fluidity. Its viscosity was 1,000 cps at 40° C. and 4,500 cps at 5° C.

EXAMPLE 4 (Skin Milk)

(1) Preparation of 18-Glycyrrhizic Acid

Part of the 18α-glycyrrhizic acid monoammonium salt prepared in Example 1 was dissolved in water, and the resulting aqueous solution was adjusted to pH 2 by the addition of hydrochloric acid. The precipitate so formed was washed with water and then dried to obtain 18α-glycyrrhizic acid in a pure form.

(2) Preparation of Skin Milk

The procedure of Example 3 was repeated except that 18α-glycyrrhizic acid was used in place of the glycyrrhizic acid composition (18α-isomer:18β-isomer=78 mole %:22 mole %). The resulting skin milk was in the form of an O/W emulsion which had been spontaneously defoamed to prefection. This skin milk presented an attractive appearance characterized by fine texture and good gloss (gloss value=92%). After 3 months' storage in a thermostatic chamber at 5° C. or 40° C., it was very stable and had excellent fluidity. Its viscosity was 3,000 cps at 5° C. and 1,000 cps at 40° C.

COMPARATIVE EXAMPLE 2

The procedure of Example 3 was repeated except that 18β-glycyrrhizic acid was used in place of the glycyrrhizic acid composition. Since the resulting skin milk had not been defoamed spontaneously, it was further defoamed by suction. However, a considerable amount of small bubbles still remained therein. The skin milk which had been defoamed by suction was stable after 3 months' storage in a thermostatic chamber at 5° C. or 40° C. Its viscosity was 1,300 cps (at 30° C.) immediately after preparation and 13,500 cps (at 30° C.) after 24 hours.

Then, the skin milks of Example 3, Example 4 and Comparative Example 2 were tested by applying thereto shear stresses of 2 and 0.4 kg/cm$^2$ with a cylinder pump type filling machine, and their viscosity and state of emulsion were examined at various stages of the test. The results thus obtained are shown in Table 4.

TABLE 4

| Skin milk | Comparative Example 2 | | Example 4 | | Example 3 | |
|---|---|---|---|---|---|---|
| Shear stress | 2 kg/cm$^2$ | 0.4 kg/cm$^2$ | 2 kg/cm$^2$ | 0.4 kg/cm$^2$ | 2 kg/cm$^2$ | 0.4 kg/cm$^2$ |
| Viscosity (cps) Immediately after preparation | 1,300 | 1,300 | 600 | 600 | 600 | 600 |
| 1 hour after preparation | 6,700 | 6,700 | 1,300 | 1,300 | 1,300 | 1,300 |
| Immediately before application of shear stress (24 hours after preparation) | 13,500 | 13,500 | 1,450 | 1,450 | 1,600 | 1,600 |
| Immediately after application of shear stress | 3,500 | 11,000 | 1,200 | 1,300 | 1,050 | 1,450 |
| 1 hour after application of shear stress | 61,500 | 14,000 | 1,350 | 1,300 | 1,350 | 1,600 |
| Immediately before re-application of shear stress (48 hours after preparation) | 23,500 | 14,500 | 1,600 | 1,400 | 1,700 | 1,900 |
| Immediately after re-application of shear stress | 7,300 | 13,000 | 1,400 | 1,300 | 1,450 | 1,350 |
| State of emulsion (after application of shear stress) | Texture and dispersed particles coarsened. | Texture and dispersed particles remained substantially unchanged. | Texture and dispersed particles remained unchanged. | Texture and dispersed particles remained unchanged | Texture and dispersed particles remained unchanged | Texture and dispersed particles remained unchanged |

It can be see from Table 4 that the skin milks of Example 4 (using 18α-glycyrrhizic acid alone) and Example 3 (using a glycyrrhizic acid composition) were only slightly influenced by the application of shear stresses. In contrast, when the skin milk of Comparative Example 2 (using 18β-glycyrrhizic acid alone) was subjected to a heavy shear stress, its viscosity showed a marked decrease and its state of emulsion tended to become poor. However, these influences marked under a mild shear stress.

EXAMPLE 5 (Skin Cream)

A. Formulation

| | | |
|---|---|---|
| 1. | Cetyl alcohol | 6 parts |
| 2. | Castor oil | 2 parts |
| 3. | Lecithin | 1 part |
| 4. | Liquid paraffin | 20 parts |
| 5. | Glycyrrhizic acid monopotassium salt composition (18α-isomer: 18β-isomer = 60.8 mole %:39.2 mole %) | 1.2 parts |
| 6. | Propylene glycol | 5 parts |
| 7. | Methylparaben | 0.2 part |
| 8. | Purified water | 64.4 parts |
| 9. | Perfume | 0.2 part |

B. Procedure

According to the above formulation, a skin cream was prepared in substantially the same manner as described in Example 1. The resulting skin cream was in the form of an O/W emulsion and presented an attractive appearance characterized by fine texture and good gloss (gloss value=90%).

It remained very stable after 6 months' storage in a thermostatic chamber at 5° C. or 45° C.

EXAMPLE 6 (Skin Cream)

(1) Preparation of 18α-Glycyrrhizic Acid Monopotassium Salt

Part of the 18α-glycyrrhizic acid prepared in Example 3 was dissolved in water, and the resulting aqueous solution was neutralized to pH 5.0 with potassium hydroxide. After the addition of acetic acid, the precipitated crystals were dried to obtain 18α-glycyrrhizic acid monopotassium salt in a pure form.

(2) Preparation of Skin Cream

The procedure of Example 5 was repeated except that 18α-glycyrrhizic acid monopotassium salt was used in place of the glycyrrhizic acid monopotassium salt composition (18α-isomer: 18β-isomer=60.8 mole %: 39.2 mole %). The resulting skin cream was in the form of an O/W emulsion and presented an attractive appearance characterized by fine texture and good gloss (gloss value=91%). It remained very stable after 6 months' storage in a thermostatic chamber at 5° C. or 45° C.

Comparative Example 3 (Skin Cream)

The procedure of Example 5 was repeated except that 18β-glycyrrhizic acid monopotassium salt was used in place of the glycyrrhizic acid monopotassium salt composition (18α-isomer: 18β-isomer=60.8 mole %: 39.2 mole %). The resulting skin cream was in the form of an O/W emulsion and presented an attractive appearance characterized by fine texture and good gloss (gloss value=80%). However, it formed a hard gel at low temperatures (of from 5° to 30° C.) and showed poor adhesion to the fingers and low affinity for the skin. When applied to the skin, this skin cream tended to slip on the skin and hence give an uneven finish. Moreover, it gave a thready and greasy feeling.

EXAMPLE 7

According to the formulation given in Table 5, a number of skin creams were prepared in substantially the same manner as described in Example 1. Some properties of the resulting creams are shown in Table 6.

TABLE 5

| Ingredient | Cream No. | | | | | | | |
|---|---|---|---|---|---|---|---|---|
| | 1 | 2 | 3 | 4 | 5 | 6 | 7 | 8 |
| Glycyrrhizic acid monoammonium salt composition [18α-isomer: 18β-isomer = 70 mole %:30 mole %] (parts) | 0.001 | 0.01 | 0.1 | 1.0 | 5.0 | 10.0 | 20.0 | 30.0 |
| Liquid paraffin (parts) | 35 | 35 | 35 | 35 | 35 | 35 | 35 | 35 |
| Stearyl alcohol (parts) | 15 | 15 | 15 | 15 | 15 | 15 | 15 | 15 |
| Methylparaben (parts) | 0.2 | 0.2 | 0.2 | 0.2 | 0.2 | 0.2 | 0.2 | 0.2 |
| Propylene glycol (parts) | 5 | 5 | 5 | 5 | 5 | 5 | 5 | 5 |
| Perfume (parts) | 0.2 | 0.2 | 0.2 | 0.2 | 0.2 | 0.2 | 0.2 | 0.2 |
| Purified water (parts) | 45 | 45 | 45 | 44 | 40 | 35 | 25 | 15 |

TABLE 6

| Property | Cream No. | | | | | | | |
|---|---|---|---|---|---|---|---|---|
| | 1 | 2 | 3 | 4 | 5 | 6 | 7 | 8 |
| Consistency (30° C.) | — | 19 | 17 | 14 | 12 | 10 | 8 | 25 |
| Texture | — | Fine | Very fine | Very fine | Very fine | Very fine | Fine | Coarse |
| Gloss value (%) | — | 80 | 95 | 95 | 95 | 90 | 70 | 60 |
| Feeling | — | Non-greasy, agreeable | Non-greasy, agreeable | Non-greasy, agreeable | Non-greasy, agreeable | Non-greasy, agreeable | Rather non-greasy | Greasy |
| Storage stability (30° C.) | Separated immediately after emulsification | Stable after 6 months | Stable after 6 months | Stable after 6 months | Stable after 6 months | Stable after 6 months | Stable after 4 months | Deposited crystals after 1 month |

It can be seen from Table 6 that excellent creams were obtained when the amount of glycyrrhizin composition used was in the range of from 0.01 to 20% by weight. When the amount was less than 0.01% by weight, the glycyrrhizin composition failed to form an emulsion. On the other hand, when the amount was greater than 20% by weight, the solubility of the glycyrrhizin composition was slightly reduced. Thus, as time went on, crystals were deposited and the gloss and texture was deteriorated.

EXAMPLE 8

The procedure of Example 7 was repeated except that 18α-glycyrrhizic acid monoammonium salt was used in place of the glycyrrhizic acid monoammonium salt composition given in Table 5. Some properties of the resulting creams are shown in Table 7.

TABLE 7

| Property | Cream No. 1 | 2 | 3 | 4 | 5 | 6 | 7 | 8 |
|---|---|---|---|---|---|---|---|---|
| 18α-Glycyrrhizic acid monoammonium salt (%) | 0.001 | 0.01 | 0.1 | 1.0 | 5.0 | 10.0 | 20.0 | 30.0 |
| Consistency (30° C.) | — | 13 | 15 | 15 | 14 | 13 | 19 | 34 |
| Texture | — | Good | Very good | Very fine | Very fine | Very fine | Fine | Coarse |
| Gloss value (%) | — | 80 | 95 | 95 | 95 | 90 | 80 | 60 |
| Feeling | — | Non-greasy, agreeable | Non-greasy, agreeable | Non-greasy, agreeable | Non-greasy, agreeable | Non-greasy, agreeable | Rather non-greasy | Greasy |
| Storage stability (30° C.) | Separated immediately after emulsification | Stable after 3 months | Stable after 6 months | Stable after 6 months | Stable after 6 months | Stable after 6 months | Stable after 3 months | Deposited crystals after 1 month |

It can be seen from Table 7 that excellent creams were obtained when the amount of 18α-glycyrrhizin used was in the range of from 0.01 to 20% by weight. When the amount was less than 0.01% by weight, the 18α-glycyrrhizin failed to form an emulsion. On the other hand, when the amount was greater than 20% by weight, the solubility of the 18α-glycyrrhizin was slightly reduced. Thus, as time went on, crystals were deposited and the gloss and texture were deteriorated.

Comparative Example 4

The procedure of Example 7 (Cream No. 4) was repeated except that 18β-glycyrrhizic acid monoammonium salt was used in place of the glycyrrhizic acid monoammonium salt composition (18α-isomer: 18β-isomer=70 mole %: 30 mole %). The resulting cream failed to be defoamed spontaneously. Thus, the same procedure was repeated again except that all the steps extending from emulsification to the discontinuance of cooling were carried out under reduced pressure. The resulting cream was in the form of an O/W emulsion which had been defoamed to perfection. Its gloss value was 80% immediately after preparation, but decreased to 55% after 1 month. Moreover, this cream formed a hard gel at low temperatures (5° C.) and showed poor adhesion to the fingers and low affinity for the skin. When applied to the skin, it tended to slip on the skin and hence given an uneven finish.

EXAMPLE 9 (Cleansing Cream)

A. Formulation

| 1. | Cetyl alcohol | 5 parts |
|---|---|---|
| 2. | Liquid paraffin | 60 parts |
| 3. | Karaya gum | 0.5 part |
| 4. | Glycyrrhizic acid dipotassium salt composition (18α-isomer: 18β-isomer = 39.3 mole %:60.7 mole %) | 3 parts |
| 5. | Methylparaben | 0.2 part |
| 6. | Purified water | 31.0 parts |
| 7. | Perfume | 0.3 part |

B. Procedure

According to the above formulation, a cleansing cream was prepared in substantially the same manner as described in Example 1. The resulting cleansing cream was in the form of an O/W emulsion and presented an attractive appearance characterized by fine texture and good gloss (gloss value=90%). It remained very stable after 6 months' storage in a thermostatic chamber at 5° C. or 45° C.

EXAMPLE 10 (Massage Cream)

A. Formulation

| 1. | Liquid paraffin | 50 parts |
|---|---|---|
| 2. | Cetyl alcohol | 5 parts |
| 3. | Xanthum gum | 0.5 part |
| 4. | Glycyrrhizic acid monoammonium salt composition (18α-isomer: 18β-isomer = 69.6 mole %: 30.4 mole %) | 3 parts |
| 5. | Methylparaben | 0.2 part |
| 6. | Purified water | 41 parts |
| 7. | Perfume | 0.3 part |

B. Procedure

According to the above formulation, a massage cream was prepared in substantially the same manner as described in Example 1. The resulting massage cream was in the form of an O/W emulsion and presented an attractive appearance characterized by fine texture and good gloss (gloss value=90%). It remained very stable after 6 months' storage in a thermostatic chamber at 5° C. or 45° C.

EXAMPLE 11 (Skin Cream)

The procedure of Example 5 was repeated except that, as shown in Table 8, 18α-glycyrrhizic acid monopotassium salt alone, 18β-glycyrrhizic monopotassium salt alone, or several glycyrrhizic acid monopotassium salt compositions consisting of both isomers in varying proportions were used in place of the glycyrrhizic acid monopotassium salt composition (18αisomer: 18β-isomer=60.8 mole %: 39.2 mole %). Some properties of the resulting skin creams are shown in Table 8.

TABLE 8

| Skin cream No. | Molar ratio of 18α-isomer to 18β-isomer | Storage stability | Texture | (gloss value) | Practical performance |
|---|---|---|---|---|---|
| 1** | 0:100 | Hardened after 2.5 months' storage at 5° C. | Fine | (70%) | Gelatin and low affinity for the skin |
| 2** | 4.0:96.0 | Hardened after 2.5 months' storage at 5° C. | Fine | (70%) | Gelation and low affinity for the skin |
| 3* | 10.3:89.7 | Stable after 6 months' storage at 5–45° C. | Fine | (80%) | High affinity for the skin |

TABLE 8-continued

| Skin cream No. | Molar ratio of 18α-isomer to 18β-isomer | Storage stability | Texture | (gloss value) | Practical performance |
|---|---|---|---|---|---|
| 4* | 30:70 | Stable after 6 months' storage at 5–45° C. | Very fine | (90%) | High affinity for the skin |
| 5* | 50.3:49.7 | Stable after 6 months' storage at 5–45° C. | Very fine | (90%) | High affinity for the skin |
| 6* | 98:2 | Stable after 6 months' storage at 5–45° C. | Very fine | (90%) | High affinity for the skin |
| 7* | 100:0 | Stable after 6 months' storage at 5–45° C. | Very fine | (90%) | High affinity for the skin |
| 8** | None | Separated after 0.5 month's storage at 45° C. | Coarse | (55%) | Rather low affinity for the skin |

*These skin creams are within the scope of the present invention.
**These skin creams are outside the scope of the present invention and are listed for purposes of comparison.

EXAMPLE 12 (Skin Cream)

The procedure of Example 5 was repeated except that the monosodium, diammonium, disodium or dipotassium salt of 18α-glycyrrhizic acid was used in place of the glycyrrhizic acid monopotassium salt composition. Each of the resulting skin creams was in the form of an O/W emulsion and presented an attractive appearance characterized by fine texture and good gloss (gloss value=90%). They remained very stable after 6 months' storage in a thermostatic chamber at 5° C. and 45° C.

EXAMPLE 13 (Skin Cream)

The procedure of Example 1 was repeated except that the diammonium, disodium, dipotassium, monopotassium or monosodium salt of 18α-glycyrrhizic acid was used in place of the glycyrrhizic acid monoammonium salt composition. Each of the resulting skin creams was in the form of an O/W emulsion and presented an attractive appearance characterized by fine texture and good gloss (gloss value=90%). They remained very stable after 6 months' storage in a thermostatic chamber at 5° C. or 40° C.

EXAMPLE 14 (Skin Milk)

The procedure of Example 3 was repeated except that xanthan gum, karaya gum, locust bean gum or casein soda was used in place of the pectin. Each of the resulting skin milks was in the form of an O/W emulsion which had been spontaneously defoamed to perfection. These skin milks presented an attractive appearance characterized by fine texture and good gloss (gloss value=90%). They remained stable after 4 months' storage in a thermostatic chamber at 5° C. or 40° C.

EXAMPLE 15 (Foundation Cream)

| A. Formulation | | |
|---|---|---|
| 1. | Liquid paraffin | 45 parts |
| 2. | Ceresin | 5 parts |
| 3. | Locust bean gum | 1.5 parts |
| 4. | Glycyrrhizic acid disodium salt composition (18α-isomer: 18β-isomer = 12.5 mole %: 87.5 mole %) | 2.0 parts |
| 5. | Methylparaben | 0.3 part |
| 6. | Titanium oxide | 2.5 parts |
| 7. | Kaolin | 1.25 parts |
| 8. | Talc | 1.1 parts |
| 9. | Yellow oxide of iron | 0.4 part |
| 10. | Purified water | 41.55 parts |

B. Procedure

According to the above formulation, a foundation cream was prepared in substantially the same manner as described in Example 1. The resulting foundation cream was in the form of an O/W emulsion and presented an attractive appearance. It remained very stable after 6 months' storage in a thermostatic chamber at 5° C. or 45° C.

EXAMPLE 16 (Foundation Cream)

The procedure of Example 15 was repeated except that 18α-glycyrrhizic acid disodium salt was used in place of the glycyrrhizic acid disodium salt composition (18α-isomer: 18β-isomer=12.5 mole %: 87.5 mole %). The resulting foundation cream was in the form of an O/W emulsion and presented an attractive appearance. It remained very stable after 6 months' storage in a thermostatic chamber at 5° C. or 45° C.

EXAMPLE 17 (Massage Cream)

The procedure of Example 10 was repeated except that, as shown in Table 9, 18α-glycyrrhizic acid monoammonium salt alone, 18β-glycyrrhizic acid monoammonium salt, or several glycyrrhizic acid monoammonium salt compositions consisting of both isomers in varying proportions were used in place of the glycyrrhizic acid monoammonium acid composition (18α-isomer: 18β-isomer=69.6 mole %: 30.4 mole %). Some properties of the resulting massage creams are shown in Table 9.

TABLE 9

| Massage cream No. | Molar ratio of 18α-isomer to 18β-isomer | Consistency (20° C.)*** Immediately After preparation | After 1 week | Texture | (gloss value) | Practical performance |
|---|---|---|---|---|---|---|
| 1** | 0:100 | 1.0 | 35 | Fine | (80%) | High viscosity, but good adhesion to the fingers and high affinity for the skin |
| 2** | 3.8:96.2 | 0.5 | 35 | Rather fine | (70%) | Rather good adhesion to the fingers and rather high affinity for the |

TABLE 9-continued

| Massage cream No. | Molar ratio of 18α-isomer to 18β-isomer | Consistency (20° C.)*** Immediately After preparation | After 1 week | Texture | (gloss value) | Practical performance |
|---|---|---|---|---|---|---|
| 3* | 10.4:89.6 | 0.5 | 16 | Fine | (80%) | Good adhesion to the fingers and good affinity for the skin |
| 4* | 50:50 | 1.0 | 13 | Very fine | (90%) | Good adhesion to the fingers and high affinity for the skin |
| 5* | 98.0:2.0 | 1.0 | 13 | Very fine | (90%) | Good adhesion to the fingers and high affinity for the skin |
| 6* | 100:0 | 1.0 | 13 | Very fine | (90%) | Good adhesion to the fingers and high affinity for the skin |
| 7** | None | — | — | — | | Separated immediately after preparation |

*These massage creams are within the scope of the present invention.
**These massage creams are outside the scope of the present invention and are listed for purposes of comparison.
***Consistency was measured using the Curd Tension Meter.

Then, the massage creams of Example 17 were tested by applying a shear stress thereto with a cylinder pump type filling machine, and their consistency and state of emulsion were examined at various stage of the test. The results thus obtained are shown in Table 10. It can be seen from this table that, when the 18α-isomer content was less than 10 mole %, a marked change in consistency was caused by the application of a shear stress. However, when the 18α-isomer content was greater than 10 mole %, its influence was less marked.

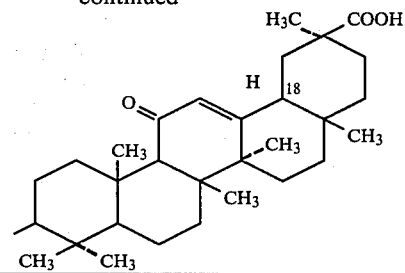

TABLE 10

| Massage cream No. | | 1** | 2** | 3* | 4* | 5* | 6* |
|---|---|---|---|---|---|---|---|
| Consistency | Immediately after preparation | 1.0 | 0.5 | 0.5 | 1.0 | 1.0 | 1.0 |
| | 1 hour after preparation | 18 | 20 | 10 | 4.5 | 5 | 5 |
| | Immediately before application of shear stress (24 hours after preparation) | 28 | 28 | 12 | 12 | 12 | 12 |
| | Immediately after application of shear stress | 5 | 0 | 5 | 6 | 7 | 7 |
| | 1 hour after application of shear stress | 25 | 31 | 12 | 7 | 7 | 7 |
| | Immediately before reapplication of shear stress (48 hours after preparation) | 28 | 39 | 15 | 11 | 10 | 10 |
| | Immediately after reapplication of shear stress | 6 | 0 | 2 | 6 | 6 | 6 |
| Decrease in consistency on application of shear stress | | Marked | Marked | Slight | Slight | Slight | Slight |
| Change of dispersed particles on application of shear stress | | Slightly coarsened | Slightly coarsened | Unchanged | Unchanged | Unchanged | unchanged |

*These massage creams were within the scope of the present invention.
**These massage creams are outside the scope of the present invention and are listed for purposes of comparison.

What is claimed is:

1. A creamy or milky oil-in-water emulsion skin cosmetic composition consisting essentially of
(a) an emulsifying agent selected from the group consisting of from 0.01 to 20% by weight based on the total weight of the skin cosmetic composition of at least one 18α-glycyrrhizin of the structural formula

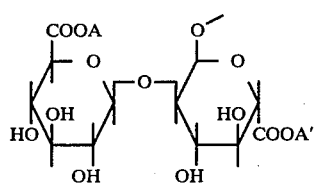

in which A and A' independently represent hydrogen atoms, sodium atoms, potassium atoms or ammonium groups, and from 0.01 to 20% by weight based on the total weight of the skin cosmetic composition of a glycyrrhizin composition consisting essentially of from 30 to 98 mole % of said 18α-glycyrrhizin and from 2 to 70 mole % of an 18β-glycyrrhizin of the structural formula

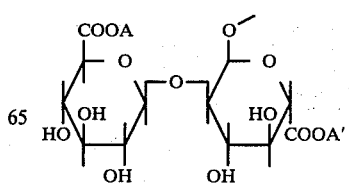

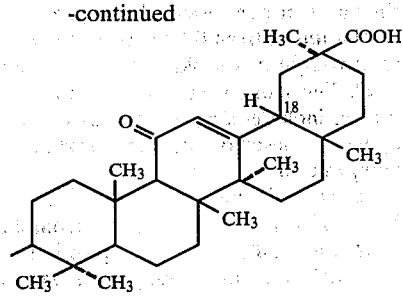

in which A and A' independently represent hydrogen atoms, sodium atoms, potassium atoms or ammonium groups;

(b) an oily substance selected from the group consisting of higher aliphatic hydrocarbons, vegetable fat, vegetable oil, animal fat, animal oil, wax, higher alcohol, higher fatty acid, straight chain ester oil and branched-chain ester oil in an amount of from 15 to 80% by weight based on the total weight of the skin cosmetic composition; and (c) water in an amount of from 10 to 90% by weight based on the total weight of the skin cosmetic composition;

said skin cosmetic composition having a pH value in the range of from 2.0 to 6.0.

2. The skin cosmetic composition of claim 1 wherein the 18α-glycyrrhizin is (3β, 18α, 20β)-20-carboxy-11-oxo-30-norolean-12-ene-3-yl-2-0-β-D-glucopyranosyl-α-D-glucopyranosiduronic acid or the monosodium, monopotassium, monoammonium, disodium, dipotassium or diammonium salt thereof.

3. The skin cosmetic composition of claim 1, wherein the 18β-glycyrrhizin is (3β, 18β, 20β)-20-carboxy-11-oxo-30-norolean-12-ene-3-yl-2-0-β-D-glucopyranosyl-β-D-glucopyranosiduronic acid or the monosodium, monopotassium, monoammonium, disodium, dipotassium or diammonium salt thereof.

4. The skin cosmetic composition of claim 1, wherein said 18α-glycyrrhizin is present in an amount of from 0.1 to 3% by weight based on the total weight of the skin cosmetic composition.

5. The skin cosmetic composition of claim 1 wherein the glycyrrhizin composition is present in an amount of from 0.1 to 3% by weight based on the total weight of the skin cosmetic composition.

6. The skin cosmetic composition of claim 1 wherein the oily substance is present in an amount of from 20 to 70% by weight, and the water is present in an amount of from 20 to 80% by weight, based on the total weight of the skin cosmetic composition.

7. The skin cosmetic composition of claim 1 which further includes an additional emulsifying agent comprising at least one water-soluble natural substance selected from the group consisting of lecithin, casein soda, pectin, xanthan gum, locust bean gum and karaya gum, in an amount of from 0.1 to 10.0% by weight based on the total weight of the skin cosmetic composition.

8. The skin cosmetic composition of claim 1 which further includes a pigment in an amount of at most 10% by weight based on the total weight of the skin cosmetic composition.

9. The skin cosmetic composition of claim 8 wherein the pigment comprises at least one inorganic pigment selected from the group consisting of titanium oxide, kaolin, yellow oxide or iron, red oxide of iron, black oxide of iron, and talc.

10. The skin cosmetic composition of claim 1, which has a pH value in the range of from 2.3 to 2.5.

11. The skin cosmetic composition of claim 1, which has a pH value in the range of from 4 to 6.

12. A creamy or milky oil in water emulsion skin cosmetic composition which consisting essentially of (a) from 0.01 to 20% by weight based on the total weight of the skin cosmetic composition of 18α-glycyrrhizin containing emulsifying agent consisting essentially of an α-acid member selected from the group consisting of (3β, 18α, 20β)-20-carboxy-11-oxo-30-norolean-12-ene-3-yl-2-0-β-D-glucopyranosyl-α-D-glucopyranosiduronic acid, and the corresponding monosodium, disodium, potassium and ammonium salts thereof, said α-acid member corresponding to the product produced by dissolving in water or alcohol a licorice root extracted 18β-glycyrrhizin containing emulsifying agent consisting essentially of a β-acid member selected from the group consisting of (3β, 18β, 20β)-20-carboxy-11-oxo-30-norloean-12-ene-3-yl-2-0-β-D-glucopyranosyl-α-D-glucopyranosiduronic acid, and the corresponding monosodium, disodium, potassium and ammonium salts thereof, heating the so dissolved β-acid member in the presence of alkali to convert the β-acid member to the corresponding alkali salt of the α-acid member, and isolating the resulting alkali salt of the α-acid member in the form of the corresponding free α-acid member as the produced product, and where said α-acid is the corresponding monosodium, disodium, potassium or ammonium salt thereafter converting the corresponding free α-acid member to such corresponding mono-salt or di-salt thereof as the produced product;

(b) from 15 to 80% by weight based on the total weight of the skin cosmetic composition of an oily substance selected from the group consisting of higher aliphatic hydrocarbons, vegetable fat vegetable oil, animal fat, animal oil, wax, higher alcohol, higher fatty acid, straight chain ester oil and branched-chain ester oil (c) from 10 to 90% by weight based on the total weight of the skin cosmetic composition of water;

said skin cosmetic composition having a pH value in the range of from 2.0 to 6.0.

13. The skin cosmetic composition of claim 12, which further includes an additional emulsifying agent comprising at least one water-soluble natural substance selected from the group consisting of lecithin, casein soda, pectin, xanthan gum, locust bean gum and karaya gum, in an amount of from 0.1 to 10.0% by weight based on the total weight of the skin cosmetic composition.

14. The skin cosmetic composition of claim 12 which further includes a pigment in an amount of at most 10% by weight based on the total weight of the skin cosmetic composition.

15. The skin cosmetic composition of claim 12 which has a pH value in the range of from 2.3 to 2.5.

16. The skin cosmetic composition of claim 12, which has a pH value in the range of from 4 to 6.

17. The skin cosmetic composition of claim 12 wherein the 18α-glycyrrhizin containing emulsifying agent consists essentially of from 0.01 to 20% by weight based on the total weight of the skin cosmetic composition of an 18α-glycyrrhizin and 18β-glycyrrhizin isomer mixture containing emulsifying agent in the form of a glycyrrhizin composition consisting essentially of from 10 to 98 mole % of said α-acid member and from 2 to 90 mole % of said β-acid member.

18. The skin cosmetic composition of claim 17 wherein said glycyrrhizin composition consists essentially of from 30 to 98 mole % of said α-acid member and from 2 to 70 mole % of said β-acid member.

19. The skin cosmetic composition of claim 17 which further includes an additional emulsifying agent comprising at least one water-soluble substance selected from the group consisting of lecithin, casein soda, pectin, xanthan gum, locust bean gum and karaya gum, in an amount of from 0.1 to 10.0% by weight based on the total weight of the skin cosmetic composition.

20. The skin cosmetic composition of claim 17 which further includes a pigment in an amount of at most 10% by weight based on the total weight of the skin cosmetic composition.

21. The skin cosmetic composition of claim 17 which has a pH value in the range of from 2.3 to 2.5.

22. The skin cosmetic composition of claim 17 which has a pH value in the range of from 4 to 6.

* * * * *